(12) United States Patent
Caldwell et al.

(10) Patent No.: US 8,163,153 B2
(45) Date of Patent: *Apr. 24, 2012

(54) TOOL FOR EXTRACTING ELECTROPHORETIC SAMPLE

(76) Inventors: Jeremy S. Caldwell, La Jolla, CA (US);
Dale R. Caldwell, Skokie, IL (US);
Leon C. Clouser, Jr., Lombard, IL (US)

( * ) Notice: Subject to any disclaimer, the term of this patent is extended or adjusted under 35 U.S.C. 154(b) by 478 days.

This patent is subject to a terminal disclaimer.

(21) Appl. No.: 12/158,208

(22) PCT Filed: Dec. 20, 2005

(86) PCT No.: PCT/US2005/046202
§ 371 (c)(1),
(2), (4) Date: Jun. 19, 2008

(87) PCT Pub. No.: WO2007/073367
PCT Pub. Date: Jun. 28, 2007

(65) Prior Publication Data
US 2009/0286326 A1 Nov. 19, 2009

(51) Int. Cl.
*G01N 27/453* (2006.01)
*G01N 27/447* (2006.01)
*B01L 3/02* (2006.01)
(52) U.S. Cl. .............. 204/462; 204/613; 73/864.11
(58) Field of Classification Search ............. 204/616, 204/613, 462, 466; 73/864.11
See application file for complete search history.

(56) References Cited

U.S. PATENT DOCUMENTS

| | | | |
|---|---|---|---|
| 1,451,610 A | 4/1923 | Gestas | |
| 2,237,213 A | 4/1941 | Brown | |
| 2,358,936 A | 9/1944 | Mathis | |
| 2,728,232 A | 12/1955 | Bremmer | |
| 3,039,500 A | 6/1962 | Goldberg | |
| 3,233,785 A | 2/1966 | Burke | |
| 3,732,734 A * | 5/1973 | Avakian | 73/864.14 |
| 3,757,585 A * | 9/1973 | Heller et al. | 73/864.18 |
| 3,839,183 A | 10/1974 | Klein et al. | |
| 3,881,527 A | 5/1975 | Shapiro | |
| 3,949,471 A | 4/1976 | Cawley | |
| 4,010,543 A | 3/1977 | Nusbaum | |
| 4,316,465 A | 2/1982 | Dotson | |

(Continued)

FOREIGN PATENT DOCUMENTS

JP  9015206  1/1997

(Continued)

OTHER PUBLICATIONS

U.S. Appl. No. 11/312,288, filed Dec. 20, 2005, Caldwell et al.

(Continued)

*Primary Examiner* — Alex Noguerola
(74) *Attorney, Agent, or Firm* — Murphy Desmond SC

(57) ABSTRACT

A gel extraction device (10) comprises a hollow cutting member (12) having cutting edge (14) at one end and a squeeze bulb (16) at the other end. In a further embodiment, the air passage between the cutting edge and the bulb has a constriction zone (20) to prevent any extracted gel from being drawn too deeply into the extractor, in another embodiment, a blow-hole in the hollow cutting member or in the squeeze bulb provides for the passage of air displaced by gel through the extractor. The blow-hole may be covered to secure the gel in the receptacle for transfer from the matrix to a sample container.

5 Claims, 2 Drawing Sheets

U.S. PATENT DOCUMENTS

| | | | |
|---|---|---|---|
| 4,471,677 A | 9/1984 | Lissot et al. | |
| 4,684,613 A | 8/1987 | Barrere et al. | |
| 4,696,298 A | 9/1987 | Higgins et al. | |
| 4,707,337 A * | 11/1987 | Jeffs et al. | 422/100 |
| 4,779,768 A | 10/1988 | St. Amand | |
| 5,032,343 A | 7/1991 | Jeffs et al. | |
| 5,125,544 A | 6/1992 | Millner et al. | |
| 5,217,591 A | 6/1993 | Gombocz et al. | |
| 5,238,651 A | 8/1993 | Chuba | |
| 5,289,727 A | 3/1994 | Earle et al. | |
| 5,343,771 A | 9/1994 | Turriff et al. | |
| 5,413,115 A | 5/1995 | Baldwin | |
| 5,476,017 A | 12/1995 | Pinto et al. | |
| 5,538,614 A | 7/1996 | Han | |
| 5,587,062 A | 12/1996 | Togawa et al. | |
| 6,342,143 B1 | 1/2002 | Minden | |
| 6,393,926 B1 | 5/2002 | Bowersox et al. | |
| 6,447,661 B1 * | 9/2002 | Chow et al. | 204/453 |
| 6,480,618 B1 | 11/2002 | Parekh et al. | |
| 6,565,728 B1 | 5/2003 | Kozulic | |
| 6,702,990 B1 | 3/2004 | Camacho et al. | |
| 7,247,275 B2 | 7/2007 | Caldwell et al. | |
| 2004/0101974 A1 | 5/2004 | Fagerstam | |

FOREIGN PATENT DOCUMENTS

| | | |
|---|---|---|
| JP | 2002307388 | 10/2002 |

OTHER PUBLICATIONS

International Preliminary Report on Patentability PCT/US05/46202 (May 20, 2008).

Revised International Preliminary Report on Patentability PCT/US05/46202 (Jun. 3, 2008).

International Search Report for PCT/US05/46202, May 20, 2008.

\* cited by examiner

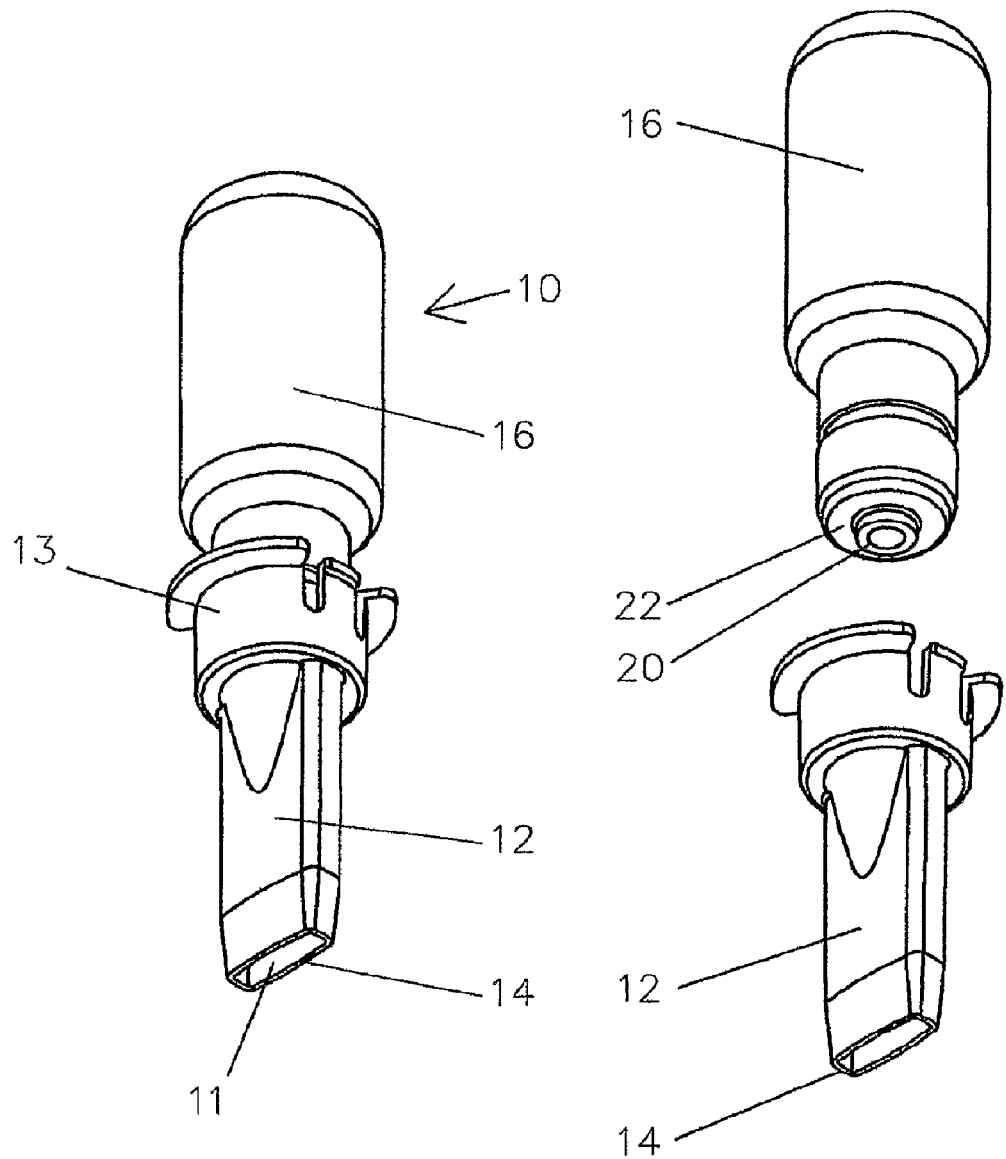

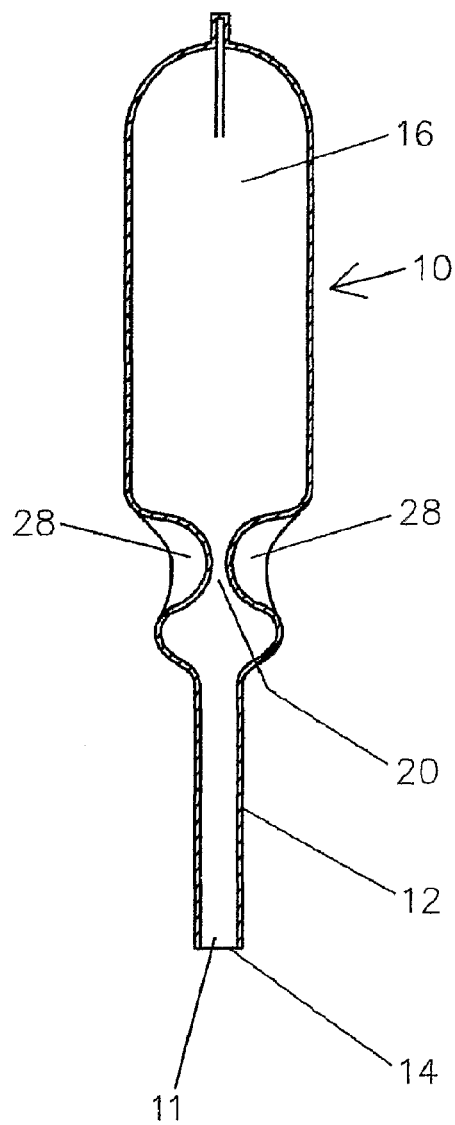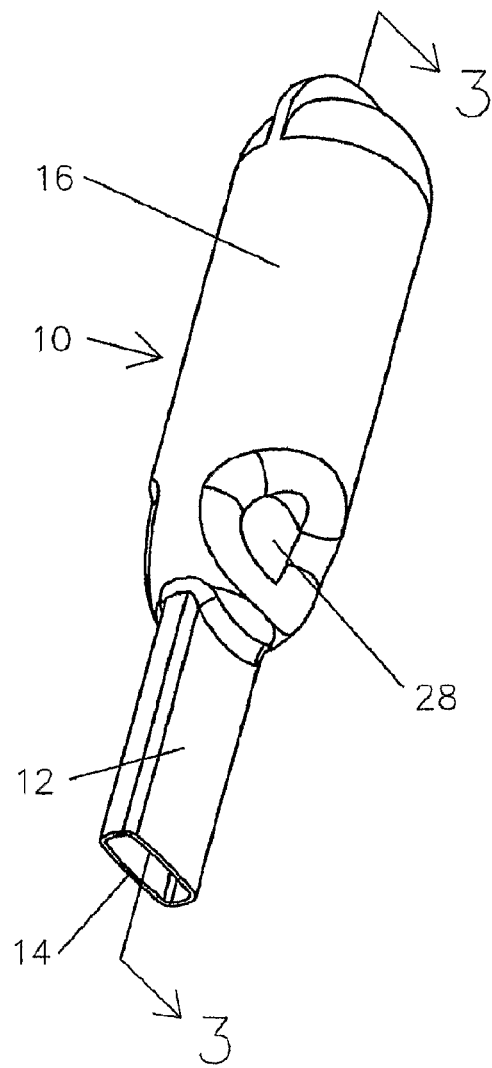

TOOL FOR EXTRACTING ELECTROPHORETIC SAMPLE

RELATED APPLICATIONS

The present application is the U.S. National Stage entry of International Patent Application PCT/US05/46202 filed 20 Dec. 2005 and claims priority from and is a continuation-in-part of U.S. patent application Ser. No. 11/312,288 filed 20 Dec. 2005, now U.S. Pat. No. 7,413,908 which claimed priority from and is a continuation-in-part of U.S. patent application Ser. No. 10/871,655 filed 21 Jun. 2004, now U.S. Pat. No. 7,247,275 issued on 24 Jul. 2007, which is also the parent application of International Patent Application PCT/US05/21572 filed 17 Jun. 2005.

BACKGROUND OF THE INVENTION

Gel electrophoresis is used extensively in the field of biotechnology to separate target biological macromolecules (biomolecules), such as DNA, RNA, or protein from a mixture of biomolecules. This analytical technique utilizes a gel matrix to separate target biomolecules for research, for preparative isolation and/or for quality testing. Target biomolecules are commonly removed from a gel polymer by extracting and processing particular sections of gel from the gel matrix. This invention provides a device for transferring a sample from the gel matrix to a container, such as an Eppendorf tube, for further processing.

The following references may relate to the technology disclosed herein: U.S. Pat. No. 6,702,990 to Camacho et al.; U.S. Pat. No. 6,565,728 to Kozulic; U.S. Pat. No. 6,393,926 to Bowersox et al.; U.S. Pat. No. 6,342,143 to Minden; U.S. Pat. No. 5,587,062 to Togawa, et al.; U.S. Pat. No. 5,476,017 to Pinto et al.; U.S. Pat. No. 5,289,727 to Earle et al.; and U.S. Pat. No. 5,217,591 to Gombocz et al. The present invention comprises a gel cutting extraction device capable of controlled one-handed cutting and simple removing of clean samples from a wide variety of electrophoretic gels.

SUMMARY OF THE INVENTION

The present invention provides a quick and easy single-handed means for extracting and transferring a sample from an electrophoretic gel for further processing. In accordance with an embodiment of the invention, a gel slice extraction device is provided that cleanly cuts a targeted gel matrix piece and retains the piece for transfer to an appropriate container, the device comprising a hollow cutting member and squeeze bulb. At one end, the hollow cutting member has a sample receptacle with a sharp cutting edge. At an opposing end of the hollow cutting member, the bulb provides for the ability to expel a gel sample from the receptacle.

In a further embodiment, the passage between the cutting edge and the bulb has a constriction zone to restrict the flow of air or of the sample in the cutting member or in the squeeze bulb. In yet another embodiment, the hollow cutting member or the squeeze bulb further comprises a blow-hole which allows air to pass through the extractor as the gel is forced into the receptacle. Once the sample is seated in the extractor, the blow-hole is closed to secure the gel in the receptacle.

BRIEF DESCRIPTION OF THE DRAWINGS

FIG. 1 illustrates an embodiment of a gel extractor comprising a hollow cutting member and a bulb.

FIG. 2 illustrates the embodiment of FIG. 1 wherein the cutting member is separated from the bulb.

FIG. 3 illustrates a cross-section of the embodiment of FIG. 4.

FIG. 4 illustrates an embodiment wherein a cutting member and a bulb are integral and a constriction zone is found in the bulb.

DETAILED DESCRIPTION OF THE INVENTION

Generally the invention is directed to a gel extraction device comprising a cutter having a connector end and an opposing cutting end defining two ends of a lumen, wherein the lumen in the cutting end defines a sample receptacle terminating in a perimeter cutting edge and the connecting end is attached to a squeeze bulb. FIG. 1 illustrates an embodiment of a gel extractor 10 comprising a hollow cutting member 12 and a squeeze bulb 16. Hollow cutting member 12 defines a lumen having a receptacle end defining a sample receptacle 11 and a connector end 13. As shown, the sample receptacle 11 is shaped to accommodate substantially rectangular shaped gel slices, which is typical of bands of biomolecules obtained by electrophoresis. Here, the walls of the sample receptacle taper gradually into a perimeter cutting edge 14 that cleanly cuts gel slices from electrophoretic gels. In an embodiment, the perimeter cutting edge 14 is between about 0.005 to 0.03 inch thickness.

Although air pressure differential is not required to extract the sample, the bulb creates the potential for the sample to be drawn too far into the extractor by excess vacuum. In FIG. 2, an optional constriction zone 20 is shown as defined by a shoulder 22 at an open end of bulb 16. By contrast, the embodiment in FIG. 3 shows dimples 28 to form optional constriction zone 20. The optional constriction zone reduces the likelihood that the sample is drawn too far into the extractor. As shown in FIG. 2, bulb 16 is capable of being detached from hollow cutting member 12. While the squeeze bulb is shown to fit into the cutting member, another embodiment comprises a hollow cutting member that is affixed inside of the bulb.

As shown in FIG. 4, the gel extractor 10 can be a one-piece device, where the bulb 16 and the hollow cutting member 12 are formed integrally. The embodiment of FIG. 4 shows dimples 28 which define an internal constriction zone 20 (see FIG. 3). The constriction zone can be found in the hollow cutting member, the bulb, or in a transition between the two. FIG. 3 provides a cross-sectional view of the integral, one-piece device having the construction zone 20 defined by dimples 28. The width of the constricted passage is variable. As an example, for a cutting width of about 0.103 inch, the constriction may range from about 0.001 to about 0.09 inch, preferably about 0.005 to about 0.08 inch. A further embodiment may have a constriction width of between about 0.04 to about 0.07 inch. The constriction zone can be a variety of shapes and sizes, including rectangular, round, square, oval, diamond, triangular or a combination, thereof. Note that cutting edge 14 is not defined by a tapering of the walls in this embodiment.

To use the extraction tool described herein, one presses the cutting edge into the gel matrix which simultaneously cuts the sample and forces the sample into the receptacle. When the tool is pulled away from the gel matrix, the sample is retained in the receptacle. One does not need to pre-squeeze the bulb, since friction is generally sufficient to hold the sample in the receptacle. However, one may squeeze the bulb slightly prior to forcing the tip into the gel, and release the bulb to create a slight vacuum during or after the cutting edge is pressed into the gel matrix. When the dimples are in the bulb, the slight vacuum can be created by squeezing the bulb at, for example, the dimples. To transfer the sample, the bulb is squeezed to create sufficient air pressure to expel the sample.

The perimeter cutting edge 14 can be positioned at a variety of angles relative to the gel, including a preferable 90 degree angle where a clean cut is easily achieved. The downward movement of the gel extraction device 10 forces the cut gel slice into the sample receptacle which is primarily retained by friction force within receptacle 11. After the cutting step is completed, gel extractor 10 is lifted away from the remaining gel matrix with the excised gel sample retained in receptacle 11.

To further process the isolated gel sample, gel extractor 10 is placed over an open container. The user then squeezes bulb 16 to increase the internal air pressure to expel the sample from sample receptacle 11 in to the container. In an embodiment, when the user releases the bulb, the squeeze bulb returns to its original shape and the extractor may be used to extract another sample. However, use of the extractor to extract multiple samples may cause contamination of the samples. Accordingly, to prevent contamination, another embodiment provides a squeeze bulb that retains the squeezed position after use, and cannot be used more than once.

Gel extractor 10 does not rely on pressure gradations to retain the gel sample. Retention is, for the most part, achieved through frictional forces between inner walls receptacle 11 and outer walls of the gel slice. Using sharp perimeter cutting edges 14 helps insure that a clean gel sample is achieved and that the gel sample is properly seated within the receptacle. Proper seating maximizes contact points between the gel sample and the walls of the receptacle 11 so that the gel sample is retained until the gel sample transfer process. However, on occasion, a part of the sample may remain outside of the sample receptacle. Generally, this does not present a problem in retaining and transferring the gel sample.

The gel extraction device 10 perimeter sharp cutting edge 14 is amenable to a wide range of dimensions. For example, where the gel extraction device 10 is used to isolate biomolecules from preparative gels, the dimensions of the device can be varied to accommodate large gel slices. Preferably, the thickness of the cutting edges 14 should not be altered since a clean cut is desirable for all gel slices whether the gel slices are isolated for further analysis of associated biomolecules or for preparative purposes. Nevertheless, the disclosed dimensions merely disclose preferred embodiments, and are not intended to limit the invention to any specified range.

In the embodiment of the gel extraction device shown, the cutting edge defines substantially a rectangle. However, additional embodiments include cutting edge that do not define rectangular cross section. Examples of cutting cross sections include, but are not limited to substantially oval and substantially circular. For the substantially rectangular cutting cross section, some preferred embodiments have an about 0.38 millimeter (mm.) to about 6.5 mm. width, with an about 2.0 mm. to about 100 mm. length. For the substantially circular cross section, some preferred embodiments have an inner diameter of about 1 mm. to about 32 mm. In a further embodiment, the substantially circular cutting edge has a diameter of about 1.5 mm. More generically, the cross-section can be expressed in surface areas. Some such embodiments have a surface area range of between 1 mm. by 1 mm. to about 32 mm. by 32 mm. It should be apparent that the above dimensions are provided for illustrative purposes, and are not meant to limit the scope of the invention.

In a further embodiment, the connector end and the opposing cutting end of the cutter are separable, so that cutting ends having differing cross sections and differing dimensions can be used. In another, embodiment, a blow-hole is formed in the hollow cutting member or in the bulb to allow air displaced by the sample to pass out of the extraction device. Once the sample is forced into the extraction device, the blow-hole may be covered by, for example a finger, to create a vacuum to assist in retaining the sample in the extraction device. To force the sample out of the extraction device, the blow-hole has to be covered so that sufficient air pressure can be created by squeezing the squeeze bulb to expel the sample.

All embodiments of the gel extraction device are preferably made entirely of plastic material, such as, but not limited to polypropylene, polyethylene, polystyrene or a mixture of plastic materials and the preferred manufacturing method is injection molding. The squeeze bulb may be made of the same materials as the rest of the extraction device. In addition, the bulb may be made of other pliable materials such as polyurethane, polyvinylchloride, and latex rubber. The type of plastic used need not be the same throughout the device. However, the invention is not limited by the materials disclosed. Any material useful for making the invention is within the scope of the invention.

Finally, all references, cited herein are hereby incorporated by reference. While the present invention has been described in considerable detail, it will be obvious to those skilled in the art that alterations may be made in the device itself or in the procedure for using the device without departing from the concept and scope of the present invention as described in the following claims.

We claim:

1. A gel extraction device comprising:
a hollow cutting member having a connector end and an opposing cutting end defining two ends of a lumen, wherein the lumen in the cutting end defines a sample receptacle terminating in a perimeter cutting edge; and
a squeeze bulb is affixed by inserting the bulb into the connector end,
wherein a constriction zone provides restricted passage between the receptacle and the squeeze bulb.

2. A gel extraction device comprising:
a hollow cutting member having a connector end and an opposing cutting end defining two ends of a lumen, wherein the lumen in the cutting end defines a sample receptacle terminating in a perimeter cutting edge; and
a squeeze bulb is affixed by inserting the connector end into the bulb,
wherein a constriction zone provides restricted passage between the receptacle and the squeeze bulb.

3. A gel extraction device comprising:
a hollow cutting member having a connector end and an opposing cutting end defining two ends of a lumen, wherein the lumen in the cutting end defines a sample receptacle terminating in a perimeter cutting edge; and
a squeeze bulb is affixed by inserting the connector end into the bulb,
wherein a constriction zone is found in the hollow cutting member and said constriction zone provides restricted passage between the receptacle and the squeeze bulb.

4. A gel extraction device comprising:
a hollow cutting member having a connector end and an opposing cutting end defining two ends of a lumen, wherein the lumen in the cutting end defines a sample receptacle terminating in a perimeter cutting edge; and
a squeeze bulb is affixed by inserting the connector end into the bulb, wherein a constriction zone is found in the squeeze bulb and said constriction zone provides restricted passage between the receptacle and the squeeze bulb.

5. A method of extracting a gel sample from an electrophoresis gel matrix with a gel extraction device comprising a hollow cutting member having a connector end and an opposing cutting end defining two ends of a lumen, wherein the lumen in the cutting end defines a sample receptacle terminating in a perimeter cutting edge and a squeeze bulb attached at the connector end, the method comprising the steps of:

pressing the perimeter cutting edge against the gel matrix to cut the gel sample, and force the sample into the sample receptacle;

pulling gel extraction device from the gel matrix to extract the gel sample in the sample receptacle; and squeezing the bulb to force the gel sample from the sample receptacle.

* * * * *